US009193711B2

(12) United States Patent
Cooperwood (10) Patent No.: US 9,193,711 B2
(45) Date of Patent: Nov. 24, 2015

(54) SERMS FOR THE TREATMENT OF ESTROGEN RECEPTOR-MEDIATED DISORDERS

(71) Applicant: Florida A&M University, Tallahassee, FL (US)

(72) Inventor: John S. Cooperwood, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 36 days.

(21) Appl. No.: 14/050,986

(22) Filed: Oct. 10, 2013

(65) Prior Publication Data

US 2014/0073656 A1    Mar. 13, 2014

Related U.S. Application Data

(63) Continuation of application No. PCT/US2012/032895, filed on Apr. 10, 2012.

(60) Provisional application No. 61/473,800, filed on Apr. 10, 2011.

(51) Int. Cl.
| C07D 403/06 | (2006.01) |
| C07D 209/30 | (2006.01) |
| C07D 473/08 | (2006.01) |
| C07D 473/34 | (2006.01) |
| C07D 473/40 | (2006.01) |

(52) U.S. Cl.
CPC ............ C07D 403/06 (2013.01); C07D 209/30 (2013.01); C07D 473/08 (2013.01); C07D 473/34 (2013.01); C07D 473/40 (2013.01)

(58) Field of Classification Search
CPC .................................................... C07D 403/06
See application file for complete search history.

(56) References Cited

U.S. PATENT DOCUMENTS

| 2,969,363 | A | 1/1961 | Schlesinger et al. |
| 4,533,493 | A | 8/1985 | Benovic et al. |
| 4,851,433 | A | 7/1989 | Kraus |
| 5,565,566 | A | 10/1996 | Olsson |
| 6,127,425 | A | 10/2000 | Tully |
| 6,395,733 | B1 | 5/2002 | Arnold et al. |
| 7,122,669 | B1 | 10/2006 | Haesslein |
| 7,208,598 | B2 | 4/2007 | Haesslein |
| 7,279,482 | B2 | 10/2007 | Dolezal et al. |
| 7,687,486 | B2 | 3/2010 | Cooperwood |
| 7,968,536 | B2 | 6/2011 | Cossrow et al. |
| 2003/0186999 | A1 | 10/2003 | Meijer et al. |
| 2005/0153989 | A1 | 7/2005 | Grotzfeld et al. |
| 2005/0187389 | A1 | 8/2005 | Milanov et al. |
| 2007/0021446 | A1 | 1/2007 | Ehlert et al. |

FOREIGN PATENT DOCUMENTS

ES        416595      *   7/1973

OTHER PUBLICATIONS

Lin and Price. Synthesis of Some 9-[2-(Diethylamino)ethyl]-6-substituted Purines as Potential Antmetabolites. Journal of Organic Chemistry. 1961. vol. 26: Abstract.

Bell et al., Synthesis, C-13 NMR, and X-ray crystal structure of N6,N9-octannethylenepurinecyclophane. Can. J. Chem. 1992. vol. 70: 186-196.

International Search Report and Written Opinion for PCT/US2012/032895 (filing date: Apr. 10, 2012) with a mailing date of Dec. 28, 2012; Applicant: Florida A&M University.

International Preliminary Report on Patentability for PCT/US2012/032895 (filing date: Apr. 10, 2012) with a mailing date of Oct. 24, 2013; Applicant: Florida A&M University.

* cited by examiner

*Primary Examiner* — Paul Zarek (74) *Attorney, Agent, or Firm* — Nilay J. Choksi; Smith & Hopen, P.A.

(57) ABSTRACT

Novel compounds for the treatment of estrogen receptor-mediated disorders, including breast cancer, and methods of treatment using the novel compounds. The novel compounds, when administered in a safe and effective amount, present extended binding to estrogen receptors in breast tissue without activating the estrogen receptors. Estrogen is blocked from binding to the estrogen receptors for an extended period of time, effectively hindering growth of breast cancer cells.

21 Claims, 8 Drawing Sheets

SERMS FOR THE TREATMENT OF ESTROGEN RECEPTOR-MEDIATED DISORDERS

CROSS-REFERENCE TO RELATED APPLICATIONS

This application is a continuation of prior filed International application, Serial Number PCT/US2012/032895 filed Apr. 10, 2012, which claims priority to U.S. Provisional Application No. 61/473,800, entitled "Small Molecules for the Treatment of Cancer", filed on Apr. 10, 2011 by the same inventor, the contents of which are hereby incorporated by reference into this disclosure.

FEDERALLY SPONSORED RESEARCH OR DEVELOPMENT

This invention was made with government support under Grant No. G 12 MD007582-28 awarded by the National Institutes of Health. The government has certain rights in the invention.

BACKGROUND OF THE INVENTION

1. Field of the Invention

This invention relates, generally, to a novel family of small molecule drugs. More particularly, it relates to selective estrogen receptor modulators for the prevention or treatment of estrogen receptor-mediated disorders.

2. Description of the Prior Art

Globally, breast cancer is the second most common cancer after lung cancer and the most common cancer for women following lung cancer. The breast cancer drug market is a steadily increasing market due to treatments which have decreased mortality and resulted in longer duration of therapy. The five-year survival rates for women with breast cancer have improved from under 70% about fifty years ago to around 90% now.

Approximately 47% of breast cancer drug sales were derived from the U.S., followed by 41% from Europe and 12% from Japan. Over the next six years the report forecasts that novel therapies, including targeted monoclonal antibodies and small-molecule inhibitors, will increasingly be used in combination with chemotherapy and hormonal therapy.

Estrogen is a hormone critical to normal human development and function. Although estrogen is the predominant "sex hormone" in women, in whom estrogen controls the development of female sex characteristics and the development and function of the reproductive system (Berkow, Beers et al. 1997), it is also found in men (Gustafsson 1998). Women produce estrogen primarily in the ovaries; however, estrogen affects a variety of physiological functions in women including body temperature regulation, maintenance of the vaginal lining, and preservation of bone density (Jordan 1998). In addition, estrogen provides additional effects that are related to its ability to modulate production of cholesterol in the liver, as demonstrated by the reduced occurrence of atherosclerosis in women compared to men due in part to the reduction of low-density lipoprotein ("LDL") (Jordan 1998). Estrogen has also been implicated in delaying and/or reducing the severity of Alzheimer's Disease (Jordan 1998).

Failure to produce estrogen has profound physiological consequences in females. Failure to produce estrogen resulting from incomplete or absent ovary development (Turner's Syndrome) causes deficiencies in the skin, bone (e.g., severe osteoporosis), and other organs severely affecting the life of the afflicted individual (Dodge 1995). In normal women, estrogen production falls sharply upon the onset of menopause, usually at about 50 years of age. The effects of the loss of estrogen production include increased atherosclerotic deposits (leading to an increased incidence of heart disease), decreased bone density (osteoporosis), and fluctuations in body temperature (Jordan 1998). Often, the effects of reduced estrogen production are addressed by hormone replacement therapy (Dodge 1995; Berkow, Beers et al. 1997; Jordan 1998).

However, estrogen also has some undesirable side effects that may lead to estrogen receptor-mediated disorders. Though supplementation of estrogen in menopausal women is associated with alleviation of the above-described unwanted indications, administration of estrogen is also associated with increased risks for breast and endometrial cancer as well as blood clots (Jordan 1998). The increased risk of endometrial cancer can be addressed by the administration of progesterone (or its synthetic analog progestin) to re-initiate menstruation and thereby shed potentially malignant cells, but many older women find this undesirable (Jordan 1998). Breast cancer, however, is by far the greater risk of estrogen replacement therapy, affecting one woman in every fifteen women between the ages of 60 and 79 (Jordan 1998).

Certain selective estrogen receptor modulators ("SERMs"), for example tamoxifen, are known for regulating agonist and/or antagonist activities in estrogen receptors. Tamoxifen, U.S. Pat. Nos. 4,851,433 and 6,127,425, both of which are hereby incorporated by reference, is an antagonist of estrogen receptors in breast tissue but an agonist of estrogen receptors in endometrial tissue. Tamoxifen is often used as the endocrine therapy for hormone receptor-positive breast cancer (i.e., tamoxifen acts as an antagonist, or anti-estrogen) in pre-menopausal women. In post-menopausal women, tamoxifen is often used as well, but frequently in combination with aromatase inhibitors, which block the conversion of androgens into estrogen. Tamoxifen is metabolized into compounds that bind to estrogen receptors in breast tissue but do not activate the estrogen receptors. Thus, estrogen is blocked from binding to the estrogen receptors, hindering growth of breast cancer cells. However, tamoxifen can act on breast cancer cells for a limited amount of time, limiting its effectiveness.

Another existing SERM for the prevention and/or treatment of estrogen receptor-mediated disorders, such as breast cancer, in postmenopausal women can be found in U.S. Pat. No. 7,687,486 to Cooperwood, which is hereby incorporated by reference.

Accordingly, what is needed is a longer-lasting drug for estrogen receptor-mediated disorders, such as breast cancer, in postmenopausal women. However, in view of the art considered as a whole at the time the present invention was made, it was not obvious to those of ordinary skill how the art could be advanced.

While certain aspects of coventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for an improved, more effective and longer-lasting drug for the prevention and/or treatment of estrogen receptor-mediated disorders is now met by a new, useful and nonobvious invention.

An embodiment of the current invention is a compound having the formula (I):

(I)

R1 is a tertiary amino group, and n is between 1 and 5, where n is a variable number of carbon atoms.

In certain embodiments, R1 may be pyrrole, and n may be 2.

In a separate embodiment, the current invention is a method of treating an estrogen receptor-mediated disorder in a mammal comprising the step of administering to a patient in need thereof an effective amount of a compound having the formula (II):

(II)

R1 is a tertiary amino group, and n is 2.

In certain embodiments, R1 may be N,N-dimethylamino.

The mammalian estrogen receptors affected by the estrogen receptor-mediated disorder may be located in breast cancer cells. As such, the disorder may be breast cancer.

in a separate embodiment, the current invention is a compound having the formula (III):

(III)

R1 is a tertiary amino group, X is a halogen or nitro group, and n is between 1 and 8.

In certain embodiments, R1 may be N,N-dimethylamino X may be fluoro, and n may be 2.

In a separate embodiment, the current invention is a method of treating an estrogen receptor-mediated disorder in a mammal comprising the step of administering to a patient in need thereof an effective amount of a compound having the formula (IV):

(IV)

R1 is a tertiary amino group, X is a halogen or nitro group, and n is between and 8.

In certain embodiments, R1 may be N,N-dimethylamino and X may be fluoro.

The mammalian estrogen receptors affected by the estrogen receptor-mediated disorder may be located in breast cancer cells. As such, the disorder may be breast cancer.

In a separate embodiment, the current invention is a compound having the formula (V):

(V)

R1 is a first tertiary amino group, R2 is a second tertiary amino group, and between 1 and 8.

In certain embodiments, R1 may be N,N-diisopropylamino, R2 may be N,N-diisopropylamino, and n may be 2.

In a separate embodiment, the current invention is a method of treating an estrogen receptor-mediated disorder in a mammal comprising the step of administering to a patient in need thereof an effective amount of a compound having the formula (VI):

(VI)

R1 is a first tertiary amino group, R2 is a second tertiary amino group, and n is between 1 and 8.

In certain embodiments, R1 may be pyrrole, R2 may be pyrrole, and n may be 2.

The mammalian estrogen receptors affected by the estrogen receptor-mediated disorder may be located in breast cancer cells. As such, the disorder may be breast cancer.

In a separate embodiment, the current invention is a compound having the formula (VII):

(VII)

R1 is a tertiary amino group.

In certain embodiments, R1 may be N,N-dimethylamino and n may be 2.

In a separate embodiment, the current invention is a method of treating an estrogen receptor-mediated disorder in a mammal comprising the step of administering to a patient in need thereof an effective amount of a compound having the formula (VIII):

(VIII)

R1 is a tertiary amino group.

In certain embodiments, R1 may be N,N-ditnethylamino and n may be 2.

The mammalian estrogen receptors affected by the estrogen receptor-mediated disorder may be located in breast cancer cells. As such, the disorder may be breast cancer.

In a separate embodiment, the current invention is a compound having the formula (IX):

(IX)

R1 is a tertiary amino group.

In certain embodiments, R1 may be pyrrole and n may be 2.

In a separate embodiment, the current invention is a method of treating an estrogen receptor-mediated disorder in a mammal comprising the step of administering to a patient in need thereof an effective amount of a compound having the formula (X):

(X)

$R_1$ is a amino group.

In certain embodiments, $R_1$ may be pyrrole and n may be 2.

The mammalian estrogen receptors affected by the estrogen receptor-mediated disorder may be located in breast cancer cells. As such, the disorder may be breast cancer.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention relates to compounds that have biological activity with respect to estrogen receptors. The invention also relates to the use of such compounds to treat diseases and disorders related to estrogen receptor activity. More particularly, the present invention provides selective estrogen receptor modulators ("SERMs") for use, for example, in treating mammalian cancers. The present invention therefore relates to the fields of medicine, medicinal chemistry, biochemistry and endocrinology.

Certain embodiments of the present invention provide compounds that have useful agonist and/or antagonist activity with respect to mammalian estrogen receptors in addition to compounds, compositions, and methods useful for treating estrogen receptor-mediated disorders in mammals. More particularly, the compounds of the present invention have been found to possess an unexpected degree of activity with respect to the alpha-isoforms of human estrogen receptor in MCF-7 breast cancer cells. Thus, the compounds, compositions, and methods described herein have utility in preventing and/or treating a wide variety of estrogen receptor-mediated disorders or a stereoisomer, enantiomer, rotomer, tautomer or a pharmaceutically acceptable salt thereof.

Certain embodiments of the present invention provide tertiary amino estrogen receptor agonist and antagonist compounds in addition to methods and compositions for treating or preventing estrogen receptor-mediated disorders. The compounds described herein have been found to have unexpected and surprising activity in modulating estrogen receptor activity. Thus, the compounds of the present invention have utility in preventing and/or treating estrogen receptor-mediated disorders, including, but not limited to, breast cancer, osteoporosis, endometrial cancers, atherosclerosis, menopause, premenstrual syndrome, and Alzheimer's disease.

Synthesis of N-phenyl-9H-purine-6-amine

Figure 1:
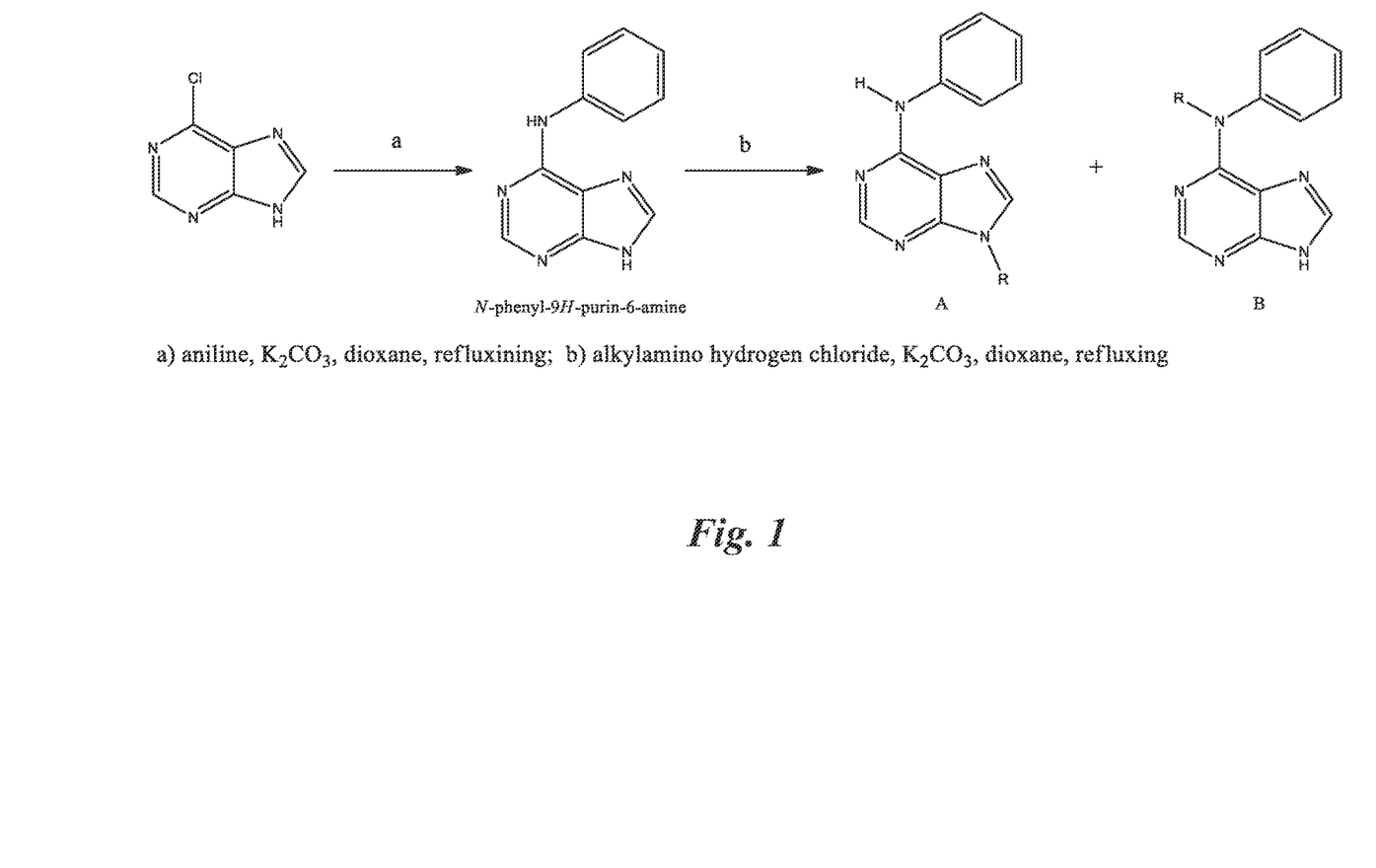
FIG. 1 is an illustration of the chemical structure of a compound of the current invention.

The general procedure for the synthesis of purine derivatives is depicted in FIG. 1. The initial compound 6-chloropurine (1.0 eq.) was mixed with aniline (1.20 eq.) and $K_2CO_3$ (2.5 eq.) in 50.0 ml dioxane. The resultant mixture was charged in 100 mL round bottom flask with a stirring bar. The mixture was refluxed overnight and monitored by TLC. After the reaction finished, the solvent was removed and the remaining residue was extracted by ethyl acetate. After removing the solvent, the resultant crude product was purified by silica gel column chromatography eluting with $CH_2Cl_2$/MeOH (5%) to provide pure titled compound.

Figure 2:
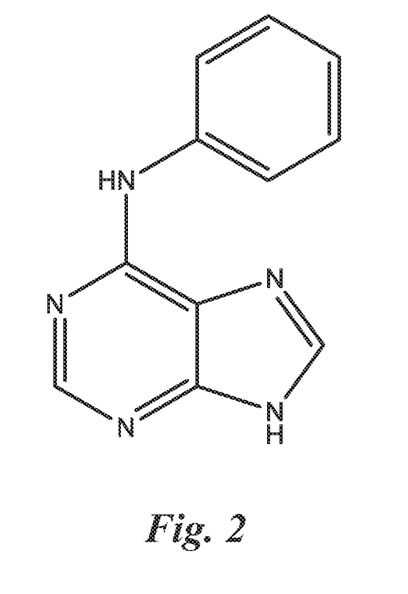
FIG. 2 is an illustration of the chemical structure of a compound of the current invention.

Using this procedure, the product of FIG. 2 was obtained as a white solid ($^1$H-NMR (300 MHz, DMSO) δ 10.27 (s, 1H), 8.44 (s, 1H), 8.40 (s, 1H), 7.94 (d, J=7.8 Hz, 2H), 7.33 (t, J=7.8 Hz, 2H), 7.04 (t, J=7.2 Hz, 1H)).

Synthesis of N-phenyl-9-alkylamino-purine-6-amine and N-phenyl-N-alkylamino-9H-purine-6-amine A mixture of 6-aniline-purine (1.0 eq.), alkylamino hydrogen chloride salt (1.10 eq.) and $K_2CO_3$ (2.5 eq.) in 50.0 ml dioxane was charged in 100 ml round flask with stirring bar. The mixture was refluxed overnight and monitored by TLC. After the reaction finished, the mixture was extracted by ethyl acetate. After removing the solvent, the result crude product was purified by silica gel column chromatography eluting with $CH_2Cl_2$/MeOH (10%) to provide pure titled compounds A and B of FIG. 1.

Figure 3A:
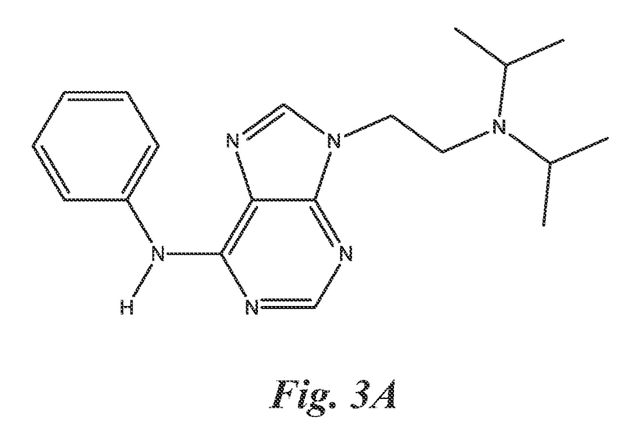
FIG. 3A is an illustration of the chemical structure of a compound of the current invention.

Using this procedure, the product of FIG. 3a was obtained as an off-white solid ($^1$H-NMR (300 MHz, DMSO) δ 9.82 (s, 1H), 8.41 (s, 1H), 8.25 (s, 1H), 7.98 (dd, J=8.9, 1.2 Hz, 2H), 7.33 (ld, J=7.8, 1.2 Hz, 2H), 7.04 (td, J=7.2, 0.9 Hz, 1H), 4.17 (t, J=6.2 Hz, 2H), 2.98 (m, 2H), 2.79 (1, J=6.2 Hz, 2H), 0.83 (d, J=6.6 Hz, 12H)).

Figure 3B:
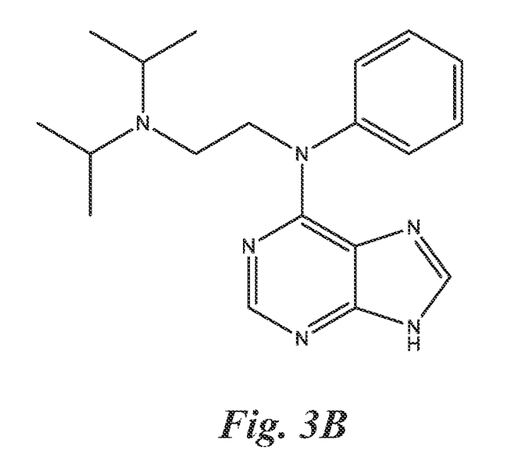
FIG. 3B is an illustration of the chemical structure of an isomer of FIG. 3A.

Using this procedure, the product of FIG. 3b as obtained as an off-white solid ($^1$H-NMR (300 MHz, CDCl$_3$) δ 8.22 (s, 1H), 8.04 (s, 1H), 7.77 (dd, 1.2 Hz, 2H), 7.33 (td, J=7.8, 1.2 Hz, 2H), 7.14 (td, J=7.2, 1.2 Hz, 1H), 4.40 (t, J=5.4 Hz, 2H), 3.01 (m, 2H), 2.97 (1, J=6.2 Hz, 2H), 0.81 (d, J=6.6 Hz, 12H)).

Figure 4A:
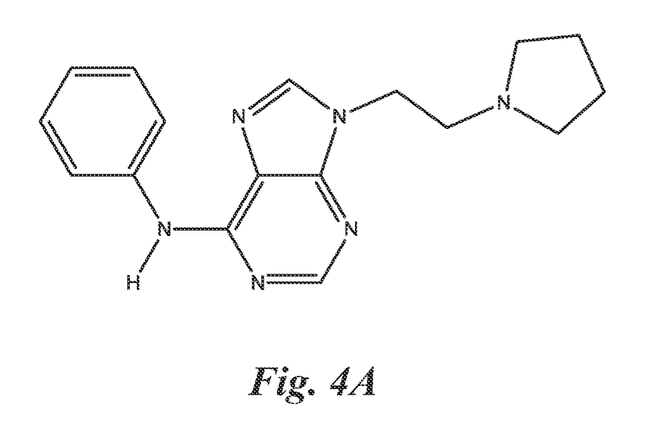
FIG. 4A is an illustration of the chemical structure of a compound of the current invention.

Using this procedure, the product of FIG. 4a was obtained as an off-white solid ($^1$H-NMR (300 MHz, CDCl$_3$) δ 8.52 (s, 1H), 8.04 (s, 1H), δ 7.86 (s, 1H), 7.81 (dd, J=8.7, 1.2 Hz, 2H), 7.38 (td, J=7.8, 1.2 Hz, 2H), 7.11 (ld, J=7.2, 0.9 Hz, 1H), 4.51 (t, J=6.6 Hz, 2H), 3.17 (t, J=6.3 2H), 2.75 (t, J=6.3 Hz, 4H), 1.88 (m, J=6.3 Hz, 4H)).

Figure 4B:
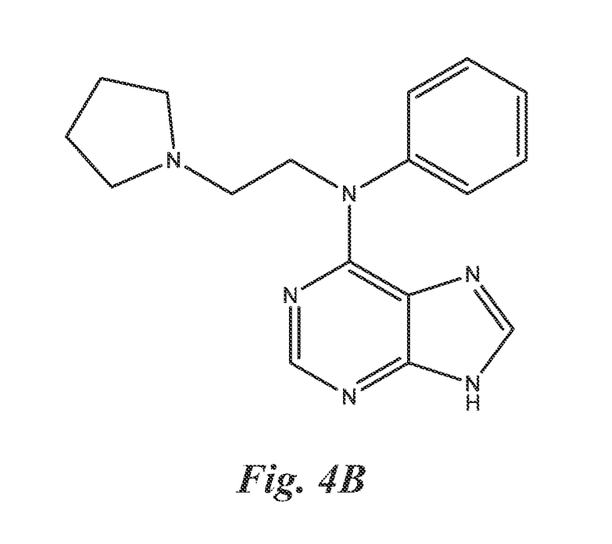
FIG. 4B is an illustration of the chemical structure of an isomer of FIG. 4A.

Using this procedure, the product of FIG. 4b was obtained as an off-white solid ($^1$H-NMR (300 MHz, CDCl$_3$) δ 8.23 (s, 1H), 8.05 (s, 1H), 7.76 (dd, J=8.4, 1.2 Hz, 2H), 7.39 (td, J=7.8, 1.2 Hz, 2H), 7.17 (td, J=7.2, 1.2 Hz, 1H), 4.51 (t, J=5.7 Hz, 2H), 3.04 (t, J=6.0 Hz, 2H), 2.55 (t, J=6.3 Hz, 4H), 1.75 (m, J=6.3 Hz, 4H)).

Figure 5A:
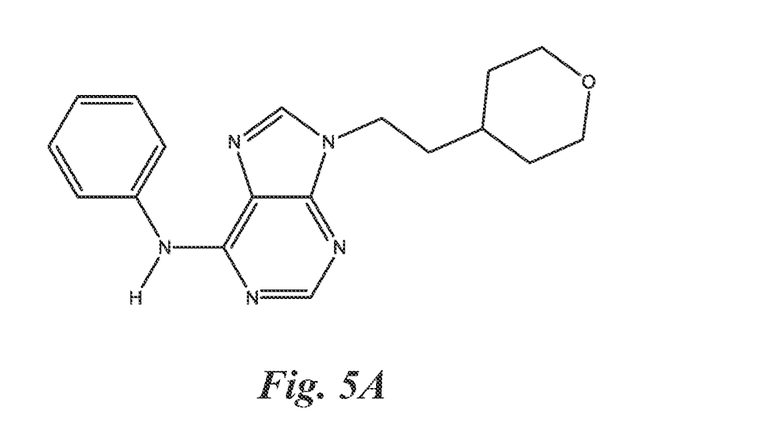
FIG. 5A is an illustration of the chemical structure of a compound of the current invention.

Using this procedure, the product of FIG. 5a was obtained as an off-white solid ($^1$H-NMR (300 MHz, CDCl$_3$) δ 8.51 (s, 1H), 7.93 (s, 1H), δ 7.79 (dd, J=8.7, 1.2 Hz, 2H), 7.36 (td, J=7.8, 2.1 Hz, 2H), 7.09 (td, J=7.2, 0.9 Hz, 1H), 4.29 (t, J=6.3 Hz, 2H), 3.65 (t, J=4.5 4H), 2.77 (t, J=6.0 Hz, 2H), 2.49 (t, J=4.5 Hz, 4H)).

Figure 5B:
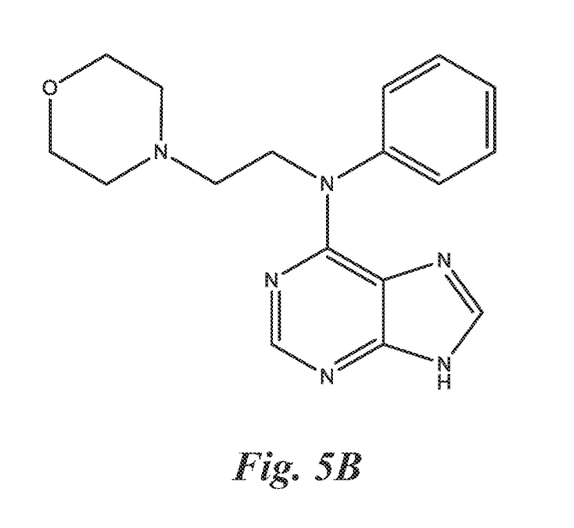
FIG. 5B is an illustration of the chemical structure of an isomer of FIG. 5A.
Figure 6:
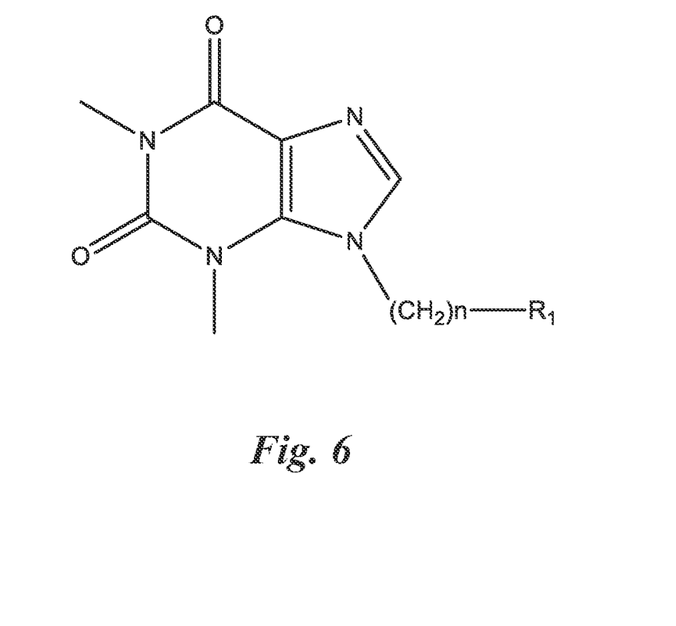
FIG. 6 is an illustration of the chemical structure of a compound of the current invention.
Figure 7:
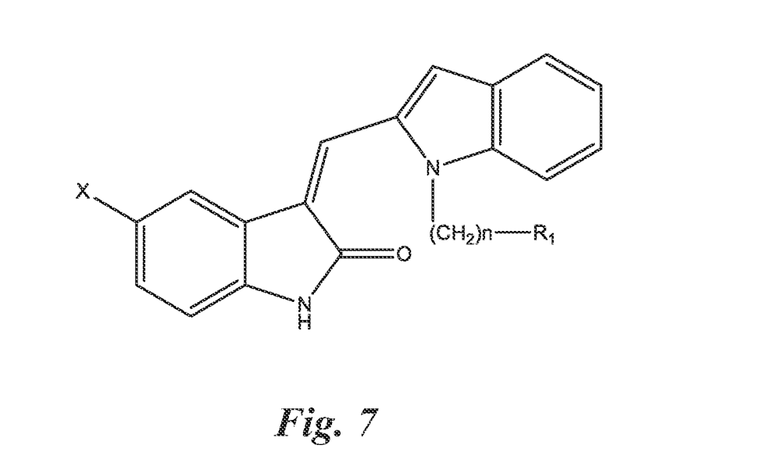
FIG. 7 is an illustration of the chemical structure of a compound of the current invention.
Figure 8:
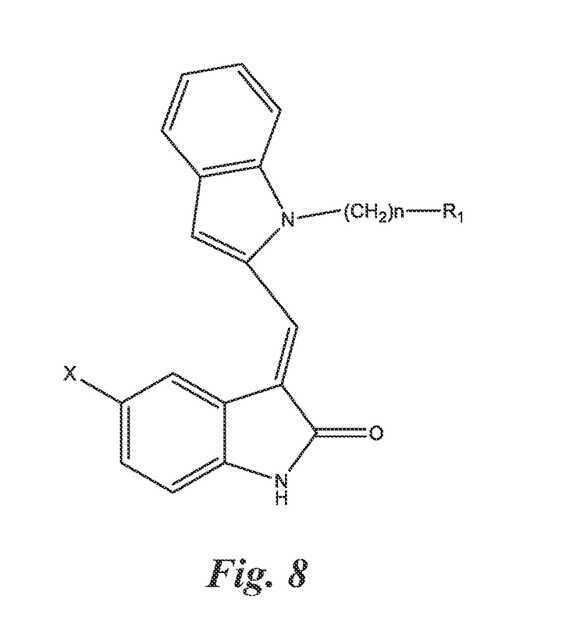
FIG. 8 is an illustration of the chemical structure of a compound of the current invention.
Figure 9:
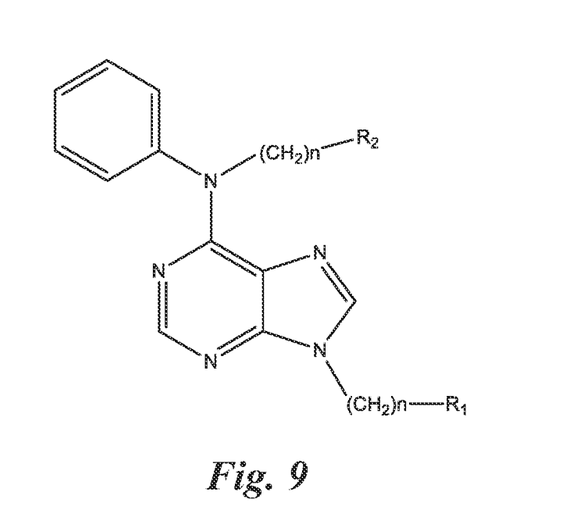
FIG. 9 is an illustration of the chemical structure of a compound of the current invention.
Figure 10:
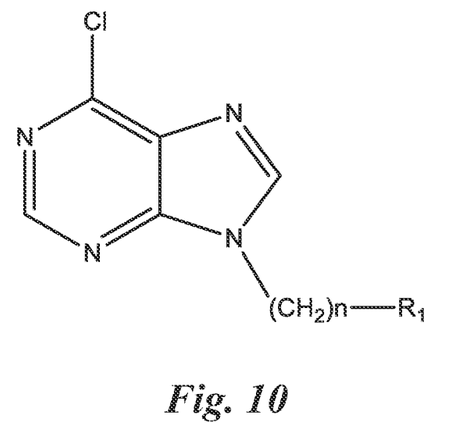
FIG. 10 is an illustration of the chemical structure of a compound of the current invention.
Figure 11:
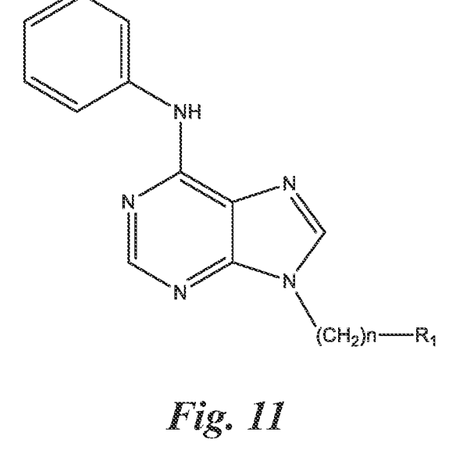
FIG. 11 is an illustration of the chemical structure of a compound of the current invention.

Using this procedure, the product of FIG. 5b was obtained as an off-white solid ($^1$H-MAR (300 MHz, DMSO) δ 8.18 (s, 1H), 8.04 (s, 1H), δ 7.75 (dd, J=8.4, 1.2 Hz, 2H), 7.40 (1, J=8.1 Hz, 2H), 7.18 (t, J=7.5 Hz, 1H), 4.50 (t, J=5.7 Hz, 2H), 3.65 (1, J=4.5 4H), 2.91 (t, J=5.7 Hz, 2H), 2.49 (t, J=4.5 Hz, 4H)).

Definitions

The term "administration" and variants thereof (e.g. "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration"

and its variants are each understood to include concurrent and sequential introduction of the compound or prodrug thereof and other agents.

As used herein, the term "tertiary amino" refers to the group -$alk_1$-N-$alk_2$ and $alk_3$ where $alk_1$ is alkylenyl or alkenyl, and $alk_2$ is alkyl or alkenyl and $alk_3$ is alkylenyl or alkenyl. The term "lower tertiary amino" refers to a tertiary amino where $alk_1$ is lower alkylenyl or lower alkenyl, and $alk_2$ is lower alkyl or lower alkenyl and $alk_3$ is lower alkyl or lower alkenyl. The term "arylaminoalkyl" refers to the group -alkylenyl-N-aryl and alkyl or aryl. The term "aralkaminoalkyl" refers to the group -alkylenyl-N-aralkyl and alkyl or aryl, where aralkyl is a lower aralkyl.

As used herein, the term "composition" is intended to encompass a product comprising the specified ingredients, in the specified amounts, as well as any product which results, directly or indirectly, from combination of the specified ingredients in the specified amounts. Generally, the specified ingredients, or pharmaceutically acceptable salts and derivatives thereof, are suitable agents for use in the diagnosis, mitigation, treatment, cure, or prevention of disease in a subject, specifically but not exclusively effective in the treatment and/or prevention of estrogen receptor-mediated disorders, including specifically the treatment and/or prevention of breast cancer, when administered in an effective amount to a subject in need thereof.

As used herein, the term "estrogen receptor" refers to any protein in the nuclear receptor gene family that binds estrogen, including, but not limited to, any isoforms or deletion mutations having the characteristics just described. More particularly, the present invention relates to estrogen receptor(s) for human and non-human mammals. Human estrogen receptors included in the present invention include the alpha and beta-isoforms (referred to herein as "estrogen receptor alpha." and "estrogen receptor beta.") in addition to any additional isoforms as recognized by those of skill in the biochemistry arts.

As used herein, the term "estrogen receptor modulator" refers to a compound that can act as an inhibitor estrogen receptor alpha enriched breast cancer cells having an $IC_{50}$ or $EC_{50}$ of no more than about 50 muM as determined using the estrogen receptor alpha enriched breast cancers proliferation assay described herein below. Representative compounds of the present invention have been discovered to exhibit antagonist activity via estrogen receptor alpha enriched breast cancer cells. Compounds of the present invention specifically exhibit an antagonist $IC_{50}$ or $EC_{50}$ with respect to estrogen receptor alpha enriched breast cancer cells of no more than about 50·mu·M, "$IC_{50}$" is that concentration of inhibitor at which 50 percent of growth or inhibition of a target such as, for example, estrogen receptor alpha enriched breast cancer cells. The term "MCF-7 cells" as used herein relates to estrogen receptor alpha enriched breast cancer cells taken from patients.

As used herein, the term "neoproliferative disease" means a neoplasm, cancer, or precancerous lesion. The neoplasm or cancer may be benign or malignant.

As used herein, "patient", "subject" and "subject in need of treatment" are used interchangeably to mean mammals in need of diagnosis or treatment for estrogen receptor-mediated disorders, such as a cancer or pre-cancer or lesion thereof.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers, such as a solvent, suspending agent or vehicle, for delivering the compound or compounds in question to the mammal. The carrier may be liquid or solid and is selected with the planned manner of administration in mind. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, liposomes, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. The carrier can also include any and all other vehicles, coatings, diluents, antibacterial and antifungal agents, isotonic and absorption delaying agents, buffers, carrier solutions, suspensions, colloids, and the like. Formulations are described in a number of sources that are well known and readily available to those skilled in the art. Except insofar as any conventional media or agent is incompatible with the active ingredient, its use in the therapeutic compositions is contemplated. For example, *Remington's Pharmaceutical Sciences* (Martin EW [1995] Easton Pa., Mack Publishing Company, 19$^{th}$ ed.) describes formulations which can be used in connection with the subject invention.

Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

As used herein, the term "precancerous" refers to cells or tissues drat have characteristics relating to changes that may lead to malignancy or cancer, such as mutations controlling cell growth and proliferation. Examples include adenomatous growths in breast and prostate tissue, or for example, conditions of dysplastic nevus syndromes, polyposis syndromes, prostatic dysplasia, and other neoplasms, whether clinically identifiable or not.

The term "prevention" is used herein to refer to the management of the factors that could lead to disease or disorder, so as to prevent the occurrence of the disease or disorder. Specifically, the disease or disorder includes, but is not limited to, estrogen receptor-mediated disorders.

A "safe and effective amount" refers to the quantity of a component or composition that is sufficient to yield a desired therapeutic response without undue adverse side effects (such as toxicity, irritation, or allergic response) commensurate with a reasonable benefit/risk ratio when used in the manner of this invention for the treatment and/or prevention of estrogen receptor-mediated disorders, including but not limited to breast cancer in a subject in need thereof.

As used herein, the term "selective estrogen receptor modulator" (or "SERM") is a compound that exhibits activity as an agonist or antagonist of an estrogen receptor (e.g., estrogen receptor alpha or estrogen receptor beta in a tissue-dependent manner. Thus, as will be apparent to those of skill in the biochemistry and endocrinology arts, compounds of the invention that function as SERMs can act as estrogen receptor agonists in some tissues such as, for example, bone, brain, and/or heart and as antagonists in other tissue types, such as, for example, the breast and/or the uterine lining.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "treatment" refers to obtaining beneficial or desired clinical results, or any measurable mitigation of disease in a subject, including resolution, reduction, halting progression, and/or slowing progression of a disease. Beneficial or desired clinical results include, but are not limited to, any one or more of the following: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, remission (whether partial or total). It is contemplated that these same benefits may apply to other estrogen receptor-mediated disorders as well. The methods of the invention contemplate any one or more of these aspects of treatment.

Therapies and Administration

Embodiments of the present invention provide compositions and methods for the prevention and/or treatment of estrogen receptor-mediated disorders, including the treatment and/or prevention of breast cancer through the modulation of MCF-7 breast cancer cells. Subjects suffering from estrogen receptor-mediated disorders can be treated by administering to the subject an effective amount of the compounds in the present invention. The compounds can be administered by any appropriate route, for example orally, intravenously, parenterally, enterally, intradermally, subcutaneously, rectally, topically and/or intranasally. The compounds of the present invention may be administered before, upon, and/or after the onset of the condition to be alleviated, and may be administered on various dosing regiments.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. For example, the dosage of a compound of the invention administered can be about 1 to about 1000 $mg/m^2$, about 1 to about 500 $mg/m^2$, about 1 to about 300 $mg/m^2$, and about 70 to about 150 $mg/m^2$. Typically, the dosage of a compound in a composition can be in the range of about 50 to about 300 $mg/m^2$ when given on a 3 week schedule, or about 10 to about 100 $mg/m^2$ when given on a weekly schedule. In addition, if given in a metronomic regimen (e.g., daily or a few times per week), the dosage may be in the range of about 1 to about 50 $mg/m^2$. It is contemplated that one of ordinary skill in the art can determine and administer the appropriate dosage of compounds disclosed in the current invention according to the foregoing considerations.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compounds used in the present invention may be administered individually, or in combination with or concurrently with one or more other compounds used in other embodiments of the present invention. Additionally, compounds used in the present invention may be administered in combination with or concurrently with other therapeutics for estrogen receptor-mediated disorders.

Embodiments of the present invention provide compounds that have useful agonist and/or antagonist activity with respect to mammalian estrogen receptors in addition to compounds, compositions, and methods useful for treating estrogen receptor-mediated disorders in mammals. More particularly, the compounds of the present invention have been found to possess a surprising degree of activity with respect to the alpha-isoforms of human estrogen receptor in MCF-7 breast cancer cells. Thus, the compounds, compositions, and methods described herein have utility in preventing and/or treating a wide variety of estrogen receptor-mediated disorders including, but not limited to, osteoporosis, breast cancer, uterine cancer, and congestive heart disease.

The current invention is described below in examples which are intended to further describe the invention without limitation to its scope.

EXAMPLE 1

MCF-7 and MDA-MB-231 human breast cancer cell lines were purchased from the National Cancer Institute. The Ishikawa human endometrial cancer cell line was purchased from SIGMA ALDRICH. All three-cell lines were cultured in phenol red-free RPMI-1640 (HYCLONE) (500 mL) supplemented with L-glutamine-dipeptide (HYCLONE) (5 mL), and 10% fetal bovine serum (ATLANTA BIOLOGICALS) (50 mL).

All three cell lines (MCF-7, MDA-MB-231, Ishikawa were maintained in exponential growth phase by sub-culturing twice weekly in 150-cm$^2$ flasks at 37° C., 95% air with 5% $CO_2$, The media was removed from the flasks, the cells washed with phosphate buffer solution (PBS) (HYCLONE), and cells were then detached using 5 mL of TrypIExpress solution (INVITROGEN) (incubation 5-10 minutes), followed by the addition of growth media. Cells were centrifuged (1,500 rpm) for 5 minutes, and resuspended in growth media at $10^5$ cells per mL. To each well of 96-well microplate, 50 μL of cell suspension was added at final density of 5,000 cells per well. After the cells were allowed to attach and grow overnight, 25 μL of 40 nM estradiol (SIGMA) was added to each well, followed by 25 μL of the different drugs treatments (compound and TAM) ranging from 400,000 nM to 0.04 nM, resulting in a final concentration of 10 nM estradiol in every well, and drug treatments ranging from 0.01-100,000 nM. Addition of the estradiol in the assays allows the conditions therein to mimic normal physiological concentration of estradiol in premenopausal women. Incubation lasted for 3 days at 37° C. air with 5% $CO_2$ followed by CellTiter-Glo assay (PROMEGA). All of the compounds were tested in triplicate for each of the cell lines. The results expressed as $IC_{50}$ (inhibitory concentration of 50%) were the averages of three data points for each concentration and were calculated using GraphPad Prism 4.0.

Using the compound of FIG. 4b, the $IC_{50}$ value (micromolar) (50% growth inhibition) in the MCF-7 breast cancer cell line was found to be 52.1. The $IC_{50}$ value (micromolar) (50% growth inhibition) in the Ishikawa endometrial cancer cell line was found to be 71.5.

The base structures of FIGS. 6-11 were developed according to a substantially similar procedure as disclosed previously herein. Each of the R groups therein can include a tertiary amino group and/or include alkyl amino and heterocyclic rings and "n" is number of carbon atoms. The R groups determine the optimal growth inhibitory activity of each compound. The R groups also allow for the development of a structure activity relationship (SAR) between each structure and its corresponding growth inhibitory activity. The extension of the carbon chain lengths also affects this inhibitory activity.

In the preceding specification, all documents, acts, or information disclosed does not constitute an admission that the document, act, or information of any combination thereof was publicly available, known to the public, part of the general knowledge in the aft, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of an antagonist modulator, it will be apparent to those skilled in the art that variations and modifications are possible without deviating from the broad spirit and principle of the present invention. It will thus be seen that the objects and advantages set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of treating an estrogen receptor-mediated disorder in a mammal, wherein said estrogen receptor-mediated disorder is breast cancer or endometrial cancer, the method con rising the step of administering to a patient in need thereof an effective amount of a compound having the formula (II):

or a stereoisomer, enantiomer, rotomer, tautomer or a pharmaceutically acceptable salt thereof, wherein $R_1$ is a tertiary amino group; and wherein n has 2 carbon atoms.

2. A method as in claim 1, wherein $R_1$ is N,N-dimethylamino.

3. A method as in claim 1, further comprising:

said mammalian estrogen receptors located in breast cancer cells;

said estrogen receptor-mediated disorder being breast cancer.

4. A compound having the formula (III):

or a stereoisomer, enantiomer, rotamer, tautomer or a pharmaceutically acceptable salt thereof,
wherein $R_1$ is a tertiary amino group;
wherein X is a halogen or nitro group; and
wherein n has from 1 to 8 carbon atoms.

5. A compound as in claim 4, wherein $R_1$ is N,N-dimethylamino, X is fluoro, and n has 2 carbon atoms.

6. A method of treating an estrogen receptor-mediated disorder in a mammal, wherein said estrogen receptor-mediated disorder is breast cancer or endometrial cancer, the method comprising the step of administering to a patient in need thereof an effective amount of a compound having the formula (IV):

or a stereoisomer, enantiomer, rotamer, tautomer or a pharmaceutically acceptable salt thereof
wherein $R_1$ is a tertiary amino group;
wherein X is a halogen or nitro group; and
wherein n has from 1 to 8 carbon atoms.

7. A method as in claim 6, wherein $R_1$ is N,N-dimethylamino and X is fluoro.

8. A method as in claim 6, further comprising:
said mammalian estrogen receptors located in breast cancer cells;
said estrogen receptor-mediated disorder being breast cancer.

9. A compound having the formula (V):

or a stereoisomer, enantiomer, rotamer, tautomer or a pharmaceutically acceptable salt thereof;
wherein $R_1$ is a first tertiary amino group;
wherein $R_2$ is a second tertiary amino group; and
wherein each n independently has from 1 to 8 carbon atoms.

10. A compound as in claim 9, wherein $R_1$ is N,N-diisopropylamino, $R_2$ is N,N-diisopropylamino, and said each n has 2 carbon atoms.

11. A method of treating an estrogen receptor-mediated disorder in a mammal, wherein said estrogen receptor-mediated disorder is breast cancer or endometrial cancer, the method comprising the step of administering to a patient in need thereof an effective amount of a compound having the formula (VI):

or a stereoisomer, enantiomer, rotamer, tautomer or a pharmaceutically acceptable salt thereof,
wherein $R_1$ is a first tertiary amino group;
wherein $R_2$ is a second tertiary amino group; and
wherein each n independently has from 1 to 8 carbon atoms.

12. A method as in claim 11, wherein $R_1$ is pyrrole, $R_2$ is pyrrole, and said each n has 2 carbon atoms.

13. A method as in claim 11, further comprising:
said mammalian estrogen receptors located in breast cancer cells;
said estrogen receptor-mediated disorder being breast cancer.

14. A method of treating an estrogen receptor-mediated disorder in a mammal, wherein said estrogen receptor-mediated disorder is breast cancer or endometrial cancer, the method comprising the step of administering to a patient in need thereof an effective amount of a compound having the formula (VIII):

(VII)

or a stereoisomer, enantiomer, rotomer, tautomer or a pharmaceutically acceptable salt thereof;

wherein $R_1$ is a tertiary amino group; and wherein n has from 1 to 8 carbon atoms.

15. A method as in claim 14, wherein $R_1$ is N,N-dimethylamino and n has 2 carbon atoms.

16. A method as in claim 14, further comprising:

said mammalian estrogen receptors located in breast cancer cells;

said estrogen receptor-mediated disorder being breast cancer.

17. A compound having the formula (IX):

(IX)

or a stereoisomer, enantiomer, rotomer, tautomer or a pharmaceutically acceptable salt thereof;

wherein $R_1$ is a tertiary amino group; and wherein n has from 1 to 8 carbon atoms.

18. A compound as in claim 17, wherein $R_1$ is pyrrole and n has 2 carbon atoms.

19. A method of treating an estrogen receptor-mediated disorder in a mammal, wherein said estrogen receptor-mediated disorder is breast cancer or endometrial cancer, the method con rising the step of administering to a patient in need thereof an effective amount of a compound having the formula (IV):

(X)

or a stereoisomer, enantiomer, rotomer, tautomer or a pharmaceutically acceptable salt thereof wherein $R_1$ is a tertiary amino group; and wherein n has from 1 to 8 carbon atoms.

20. A method as in claim 19, wherein $R_1$ is pyrrole and n has 2 carbon atoms.

21. A method as in claim 19, further comprising:

said mammalian estrogen receptors located in breast cancer cells;

said estrogen receptor-mediated disorder being breast cancer.

* * * * *

UNITED STATES PATENT AND TRADEMARK OFFICE
CERTIFICATE OF CORRECTION

| | | |
|---|---|---|
| PATENT NO. | : 9,193,711 B2 | Page 1 of 1 |
| APPLICATION NO. | : 14/050986 | |
| DATED | : November 24, 2015 | |
| INVENTOR(S) | : John S. Cooperwood | |

It is certified that error appears in the above-identified patent and that said Letters Patent is hereby corrected as shown below:

In the Claims:

Column 14, Claim 1, Line 40 should read:

method comprising the step of administering to a patient in

Column 18, Claim 19, Line 8 should read:

method comprising the step of administering to a patient in

Signed and Sealed this
Fifth Day of April, 2016

Michelle K. Lee
*Director of the United States Patent and Trademark Office*